United States Patent [19]

Hofen et al.

[11] 4,088,676

[45] May 9, 1978

[54] PROCESS FOR THE PREPARATION OF ORGANIC SOLUTIONS OF PERCARBOXYLIC ACIDS

[75] Inventors: Willi Hofen, Rodenbach; Günter Prescher, Hanau; Gerd Siekmann; Günter Wolf, both of Leverkusen, all of Germany

[73] Assignees: Bayer Aktiengesellschaft, Leverkusen; Deutsche Gold- und Silber-Scheideanstalt vormals Roessler, Frankfurt am Main, both of Germany

[21] Appl. No.: 678,825

[22] Filed: Apr. 28, 1976

[30] Foreign Application Priority Data

Apr. 30, 1975 Germany .................. 2519293

[51] Int. Cl.$^2$ .......................... C07C 179/10
[52] U.S. Cl. .................. 260/502 R; 203/14; 203/99; 203/98; 203/DIG. 6; 203/91
[58] Field of Search .......... 260/502 R; 203/14, 98, 203/99; 423/548, 587, 588, 589

[56] References Cited

U.S. PATENT DOCUMENTS

| | | | |
|---|---|---|---|
| 2,741,584 | 4/1956 | Holmes et al. | 203/98 |
| 2,814,641 | 11/1957 | Phillips et al. | 260/502 R |
| 3,043,666 | 10/1962 | Siwinski | 423/589 |
| 3,284,491 | 8/1966 | Korath et al. | 260/502 R |
| 3,341,297 | 12/1967 | MacLean et al. | 423/587 |
| 3,755,185 | 9/1973 | Woldmann | 423/584 |

FOREIGN PATENT DOCUMENTS

| | | | |
|---|---|---|---|
| 1,048,569 | 1/1959 | Germany | 260/502 R |
| 2,312,280 | 9/1974 | Germany | 260/502 R |
| 2,262,970 | 7/1974 | Germany | 260/502 R |

Primary Examiner—Bernard Helfin
Assistant Examiner—Warren B. Lone
Attorney, Agent, or Firm—Burgess, Dinklage & Sprung

[57] ABSTRACT

A process for the continuous preparation of organic solutions of percarboxylic acids by reaction of an aqueous solution of hydrogen peroxide with the corresponding carboxylic acid in the presence of an acid, water-soluble catalyst which boils above 160° C, extraction of the percarboxylic acid from the resulting reaction mixture using an organic solvent which is immiscible with water, reconcentration of the raffinate, which essentially contains hydrogen peroxide and the acid catalyst, by distilling off water in a distillation column and recycle of the raffinate, concentrated in this way, into the reaction with the carboxylic acid. The raffinate is divided into two partial streams in a ratio of 1 to 25:1. The raffinate is fed to a distillation column which is operated under reduced pressure and which has at least two take-off weirs as tray inserts, the first take-off weir being at least two theoretical plates above the sump phase, the second take-off weir being arranged at least two theoretical plates above the first take-off weir and the section of column between the second take-off weir and the top of the column having at least two theoretical plates. The larger partial stream of the raffinate is passed into the column below the first take-off weir and the smaller partial stream is passed into the column below the second take-off weir. Water is removed at the top of the distillation column. A first side stream, which essentially contains the hydrogen peroxide from the small partial stream of the raffinate from the extraction, is withdrawn from the second take-off weir and is a 2 to 40% strength by weight aqueous solution of hydrogen peroxide, which is optionally fed, together with the larger partial stream of the raffinate from the extraction, into the column below the first take-off weir. A second side stream is withdrawn from the first take-off weir and is an aqueous solution of the acid catalyst which optionally can be further worked up and re-used. The re-concentrated aqueous solution of hydrogen peroxide and acid catalyst, withdrawn as a sump product from the distillation, is recycled into the reaction with carboxylic acid. A third side stream can be taken from a third take-off weir which is arranged not more than 2 theoretical plates below the first take-off weir.

20 Claims, 4 Drawing Figures

PROCESS FOR THE PREPARATION OF ORGANIC SOLUTIONS OF PERCARBOXYLIC ACIDS

The following applications are related to the process hereof for production of propylene oxide as being directed to aspects of the process, some of which are disclosed herein.

| German Serial No. | U.S. Atty's Docket No. | U.S. Serial No. |
|---|---|---|
| P 25 19 288.5 | Bayer 2883 | 678,819 |
| P 25 19 300.4 | Bayer 2884 | 678,820 |
| P 25 19 299.8 | Bayer 2885 | 678,821 |
| P 25 19 298.7-42 | Bayer 2886 | 678,822 |
| P 25 19 297.6 | Bayer 2887 | 678,823 |
| P 25 19 295.4 | Bayer 2888 | 678,824 |
| P 25 19 292.1-42 | Bayer 2890 | 678,826 |
| P 25 19 291.0-42 | Bayer 2891 | 678,827 |
| P 25 19 289.6 | Bayer 2892 | 678,828 |
| P 25 19 297.4 | Bayer 2893 | 678,829 |

All of the German applications were filed Apr. 30, 1975. Those applications are incorporated herein by reference.

The present invention relates to an improved process for the preparation of organic solutions of percarboxylic acids.

As is known, percarboxylic acids in organic solution are selective oxidising agents. They can be employed, for example, for the epoxidation of olefines (D. Swern, "Organic Peroxides", Wiley, Interscience, 1971, volume 2, page 355–534).

Recently, processes for the preparation of organic solutions of percarboxylic acids have been disclosed which are based on the extraction, with an organic solvent, of the reaction mixture which is formed when aqueous hydrogen peroxide is reacted with carboxylic acid in the presence of an acid catalyst and which essentially consists of the carboxylic acid employed, the corresponding percarboxylic acid, unreacted hydrogen peroxide and the acid catalyst (DOS (German Published Specification) No. 1,048,569, DOS (German Published Specification) No. 2,141,156 and DOS (German Published Specification) No. 2,312,281).

The reaction of carboxylic acid with hydrogen peroxide in the presence of an acid catalyst proceeds as an equilibrium reaction in accordance with the following equation, in which RCOOH denotes a carboxylic acid and RCOOOH denotes a percarboxylic acid:

$$RCOOH + H_2O_2 \underset{}{\overset{acid\ catalyst}{\rightleftarrows}} RCOOOH + H_2O \qquad (1)$$

Consequently, the reaction cannot go to completion with respect to the formation of percarboxylic acid. Accordingly, when the reaction mixture is extracted in order to isolate an organic solution of percarboxylic acid, the unreacted hydrogen peroxide, in addition to the acid, water-soluble catalyst, remains in the raffinate.

In some of these extraction processes for the preparation of percarboxylic acid, the raffinate is discarded (see DOS (German Published Specification) No. 2,262,970, page 2, first complete paragraph). In another known process, the water-soluble acid catalyst is recovered from the raffinate, by reconcentration or distillation, after the hydrogen peroxide contained therein has been destroyed (DOS (German Published Specification) No. 2,312,281, page 5, 3rd paragraph).

According to the process of DOS (German Published Specification) No. 2,262,970, the raffinate is worked up for re-use by reconcentration by distillation. In this working up by distillation, the amount of water, which essentially is introduced with the feed products and formed during the reaction, is removed so that the valuable hydrogen peroxide and catalyst fractions contained in the raffinate can be recycled in the correct concentration. Thus, when this process is actually carried out continuously, a continuous circulation of an aqueous solution of hydrogen peroxide and acid catalyst is set up. However, the yield of percarboxylic acid, relative to hydrogen peroxide employed, decreases continuously as the operating period of the circulation process lengthens. A possibility for preventing this reduction in yield consists in withdrawing a small part of the aqueous circulating solution from the process from time to time or continuously and replacing it by fresh circulating solution mixed from pure feed products (DOS (German Published Specification) No. 2,262,970, page 4, 2nd paragraph). The result of this procedure of continuously exchanging a specific amount of the circulating solution for fresh products is, of course, that a corresponding loss of hydrogen peroxide and acid catalyst arises.

A process has now been found for the continuous preparations of organic solutions of percarboxylic acids especially monopercarboxylic by reaction of an aqueous solution of hydrogen peroxide with the corresponding carboxylic acid in the presence of an acid, water-soluble catalyst which boils above 160° C, extraction of the percarboxylic acid from the resulting reaction mixture using an organic solvent which is immiscible with water, reconcentration of the raffinate, which essentially contains hydrogen peroxide and the acid catalyst, by distilling off water in a distillation column and recycle of the raffinate, reconcentrated in this way, into the reaction, which is characterised in that (a) the raffinate is divided into two partial streams in a ratio of 1 to 25:100 and (b) fed to a distillation column which is operated under reduced pressure and which has at least two take-off weirs as tray inserts, the first take-off weir being at least two theoretical plates above the sump phase, the second take-off weir being arranged at least two theoretical plates above the first take-off weir and the section of column between the second take-off weir and the top of the column having at least two theoretical plates, (c) the larger partial stream is passed into the column below the first take-off weir and the smaller partial stream is passed into the column below the second take-off weir, (d) water is removed at the top of the distillation column, (e) a first sidestream, which contains virtually all of the hydrogen peroxide from the smaller partial stream of the raffinate from the extraction, is withdrawn from the second take-off weir and is a 2 to 40% strength by weight aqueous solution of hydrogen peroxide, which is optionally fed, together with the larger partial stream of the raffinate from the extraction, into the column below the first take-off weir, (f) a second sidestream is withdrawn from the first take-off weir and is an aqueous solution of the acid catalyst which optionally can be further worked up and re-used, and (g) the reconcentrated aqueous solution of hydrogen peroxide and acid catalyst, withdrawn as the sump product from the distillation, is recycled into the reaction with the carboxylic acid.

The process according to the invention makes it possible to prevent the loss of hydrogen peroxide which arises with a circulation exchange according to the state of the art. At the same time, the high yield of percarboxylic acid, relative to hydrogen peroxide employed, which exists at the start of the reaction, is maintained during the whole of the continuous process.

Examples of aliphatic carboxylic acids which can be used are: formic acid, acetic acid, propionic acid, butyric acid, isobutyric acid, valeric acid, trimethylacetic acid, caproic acid, heptylic acid, caprylic acid, pelargonic acid, capric acid, undecanoic acid, lauric acid, myristic acid, pentadecanoic acid, palmitic acid, stearic acid, arachic acid, fluoroacetic acid, trifluoroacetic acid, chloroacetic acid, dichloroacetic acid, trichloroacetic acid, α-chloropropionic acid, α-fluoropropionic acid, β-chloropropionic acid, succinic acid, glutaric acid, adipic acid, suberic acid, azelaic acid and sebacic acid. Cycloaliphatic carboxylic acids which may be mentioned are cyclopentanecarboxylic acid, cyclohexanecarboxylic acid, cycloheptanecarboxylic acid, cyclohexane-1,3-dicarboxylic acid and cyclohexane-1,4-dicarboxylic acid. Examples of aromatic carboxylic acids which can be used are benzoic acid, p-chlorobenzoic acid, phthalic acid, naphthalenecarboxylic acid, benzene-1,3-dicarboxylic acid and benzene-1,4-dicarboxylic acid.

Aliphatic carboxylic acids with 1 to 4 carbon atoms, such as formic acid, acetic acid, propionic acid, n-butyric acid and isobutyric acid, are particularly suitable for the process according to the invention. Propionic acid is very particularly suitable.

Suitable acid, water-soluble catalysts are sulphuric acid, phosphoric acid, phosphonic acids, phosphinic acids, acid salts of sulphuric acid or phosphoric acid, sulphonic acids, chlorinated and fluorinated sulphonic acids or mixtures of these catalysts, in so far as their boiling point is above 160° C.

Catalysts which may be mentioned individually are sulphuric acid, sodium bisulphate, potassium bisulphate, methanesulphonic acid, ethanesulphonic acid, propanesulphonic acid, butanesulphonic acid, isobutanesulphonic acid, benzenesulphonic acid, toluenesulphonic acid, trifluoromethanesulphonic acid, 1-fluoroethanesulphonic acid, perfluoroethanesulphonic acid, perfluoropropanesulphonic acid and perfluorobutanesulphonic acid. Sulphuric acid is preferably used. In particular cases, acid catalysts having a boiling point below 160° C can still be suitable for the process according to the invention.

Suitable extraction agents for the percarboxylic acid are all solvents which are not miscible with water and which are virtually inert towards hydrogen peroxide, the percarboxylic acid and the acid catalyst. For example, aliphatic, cycloaliphatic and aromatic hydrocarbons, chlorinated hydrocarbons and esters of carboxylic acids are suitable. The number of carbon atoms in these solvent compounds is generally 1 to 20, preferably 1 to 10. Suitable extraction agents are, for example, n-pentane, isooctane, cyclohexane, benzene, toluene, xylene, methylene chloride, chloroform, 1,2-dichloroethane, 1,2-dichloropropane, methyl acetate, ethyl acetate, n-propyl acetate, isopropyl acetate, n-butyl acetate, isoamyl acetate, methyl propionate, ethyl propionate, propyl propionate and butyl propionate, as well as chlorobenzene. Chlorinated hydrocarbons, such as methylene chloride or dichloroethane, and aromatic hydrocarbons, such as benzene, are preferably used. Benzene is preferably used as the extraction agent for the process according to the invention.

The feed molar ratio of aqueous hydrogen peroxide to carboxylic acid for the reaction step can be varied within wide limits. For example, the ratio of hydrogen peroxide to carboxylic acid is 0.5 to 30:1. The molar ratio of hydrogen peroxide to carboxylic acid which is selected for the reaction is preferably from 0.8 to 1.5:1, preferentially from 0.9 to 1.2:1.

The concentration of the aqueous hydrogen peroxide used is generally less than 60% by weight. The reaction of the solution of hydrogen peroxide, containing the aqueous acid catalyst, with the carboxylic acid can be carried out in very diverse reaction vessels. For example, the customary reaction tubes of varying diameter and varying length and also loop reactors and reaction loops as well as stirred kettles are suitable. The reaction temperature is generally between 10° and 70° C. Appropriately the reaction is carried out below 60° C. Temperatures below 45° C are particularly advantageous for the reaction. It is very particularly appropriate to maintain reaction temperatures of 30° to 40° C.

The pressure is not important for the reaction of the carboxylic acid with hydrogen peroxide and the acid catalyst, so the reaction can be carried out at normal pressure, elevated pressures or at reduced pressure. In general it is appropriate to work at pressures below 1.1 bars. The extraction of the reaction mixture from the reaction of carboxylic acid and hydrogen peroxide is generally carried out in such a way that percarboxylic acid and carboxylic acid are extracted as completely as possible, so that the raffinate contains virtually all the unreacted hydrogen peroxide and the water-soluble acid catalyst. However, it is also possible to carry out the extraction less completely and to process further the resulting raffinate according to the invention. Extraction units which can be used are the known extraction systems with which a multi-stage countercurrent extraction is possible. For example, mixer/settlers, sieve tray extractors, pulsed sieve tray columns or spray columns are suitable. However, it is also possible to use single stage or multi-stage centrifugal extractors. The temperature for the extraction can be varied within wide limits. In general, the extraction is carried out at temperatures of 10° to 70° C. Appropriately, the temperature selected is the same as that used for the production of the percarboxylic acid by reaction of carboxylic acid with hydrogen peroxide. The pressure inside the extraction unit is not decisive. Thus, the reaction can be carried out at normal pressure or at elevated pressures.

The raffinate is reconcentrated by distilling the entire raffinate or part of the raffinate in a manner which is in itself known, for example according to the process of DOS (German Published Specification) No. 2,262,970. Thus, it is possible (as described in DOS (German Published Specification) No. 2,262,970) to pass only the raffinate or a part thereof into the distillation unit. However, a procedure in which the fresh feed of hydrogen peroxide required for the process is passed, in addition to the raffinate or to a part thereof, into the distillation is also possible. If this procedure is followed, the fresh hydrogen peroxide can be passed in different ways into the distillation unit for reconcentration of the raffinate. The fresh $H_2O_2$ can be admixed to the raffinate from the extraction. It can also be added to the larger partial stream which, according to the process of the invention, is obtained after the raffinate has been divided. However, it is also possible to pass the hydrogen peroxide directly into the distillation unit. In general, all of the fresh hydrogen peroxide is passed into the distillation column below the first take-off weir. The feed is preferably at that point in the column at which the concentration in the distillation column is closest to that of the product fed into the distillation.

The division, according to the invention, of the raffinate into two partial streams according to process step (a) is generally made in a ratio of 1 to 25:100. The ratio of the partial streams is frequently 2 to 8:100, preferably 4 to 6:100.

The concentration of hydrogen peroxide in the raffinate can be varied within wide limits. In general, the raffinate contains 5 to 25, usually 6 to 15, % by weight of hydrogen peroxide. The concentration of acid catalyst in the raffinate depends on the nature of the acid catalyst. In general, the concentration of acid catalyst in the raffinate is 10 to 50, usually 12 to 40, % by weight.

Fractionation columns of customary design, which have at least 6 theoretical plates and which have been provided with at least two take-off weirs, are suitable for the distillation according to step (b) of the process according to the invention. In general, columns with up to 150 theoretical plates can be used. Suitable distillation columns preferably have about 9 to 60, preferentially about 12 to 30, theoretical plates. In general, the take-off weirs can be fitted to any fractionation column. A take-off weir is understood as a tray insert constructed in such a way that the reflux from the part of the column located above such a tray insert does not pass through this tray insert into the part of the column located below the tray insert. Rather, the reflux is withdrawn as a sidestream from the column above a tray insert of this type. However, the vapours from the part of the column below a take-off weir can continue to flow upwards. In industry, these special tray inserts, which are designated take-off weirs, are so designed, for example, that there is, on the tray insert, at least one passage for the vapours, which is provided with a rim. Of course, it is also possible to provide several passages of this type. Appropriately, a roof-shaped or hat-shaped device is fitted above such a passage in order to prevent the reflux being able to continue to flow downwards. In detail, all the customary embodiments are possible for the construction of weirs of this type. For example, the take-off weirs can be fitted into the fractionation column, for example as a replacement for a bubble cap tray, or resort is made to appropriate manufactured embodiments of distillation columns of this type.

With regard to the arrangement of the take-off weirs inside the column, the section of the column which extends from the sump phase up to the first take-off weir is, for example 2 to 50, preferably 3 to 20, preferentially 4 to 10, theoretical plates. The second take-off weir is fitted, for example, 2 to 50, preferably 3 to 20, preferentially 4 to 10, theoretical plates above the first take-off weir. The section of the column from the second take-off weir to the top of the column generally has 2 to 50 theoretical plates. Preferably, this part of the column is so designed that its separation effect is from 3 to 20, preferably 4 to 10, theoretical plates. The column can optionally have a third take-off weir, which is arranged below the first take-off weir. A third take-off weir of this type is generally so arranged that the distance from the third up to the first take-off weir is not more than 2 theoretical plates. Usually, a third take-off weir will be so arranged that it is located directly below the first take-off weir.

The length of the three sections of the column which extend from the sump up to the first take-off weir, from the first up to the second take-off weir and from the second take-off weir up to the top of the distillation column can vary independently of one another in the indicated ranges, relative to the number of theoretical plates. Preferably, the column sections are fitted, independently of one another, with in each case, 3 to 20, preferentially 4–10, theoretical plates. For example, in a bubble cap tray column with 18 theoretical plates, the section of the column from the sump up to the first take-off weir has 5 theoretical plates, the section from the first up to the second take-off weir has 8 theoretical plates and the section of the column from the second take-off weir up to the top of the distillation column has 5 theoretical plates. The three sections of the column can also be so arranged that their efficiencies (number of theoretical plates) are in a ratio of 1:1:1.

To carry out step (c) of the process according to the invention, the smaller partial stream of the raffinate is passed into the part of the column which is limited by the first and the second take-off weir. In general, the feed point for the smaller partial stream of the raffinate is located as far as possible directly below the second take-off weir. However, the smaller partial stream can also be passed into the column lower down, but still above the first take-off weir. It can be appropriate to take special precautions so that substantial amounts of the small partial stream are not thrown upwards through the second take-off weir by the streams of vapour. The larger partial streams of the raffinate is passed into the column below the first take-off weir, but below the third take-off weir if a third take-off weir should be present. With this proviso, any desired point can be selected at the feed point. However, it is appropriate to pass in the larger partial stream at the correct concentration, that is to say at the zone in the column in which the concentration of the feed is closes to that in the column. Frequently, this zone is in the vicinity of the sump zone.

BRIEF DESCRIPTION OF DRAWINGS

Referring to the drawings.

In general, a distillation column which is provided with an evaporator unit is used to reconcentrate the raffinate The customary columns, which are fitted with the tray inserts described, can be used as the distillation column. For example, packed columns or trayed columns are suitable. Customary equipment, such as circulation reboilers, falling flow evaporators and thin layer evaporators, are also suitable as the evaporator. Preferably, falling flow evaporators or thin layer evaporators are used.

The distillation is carried out under reduced pressure. It is appropriate to work at pressures below 250 mm Hg.

In many cases it is particularly advantageous to use pressures below 150 mm Hg. The temperature in the evaporator appropriately depends on the composition of the sump product and on the pressure. In general, the conditions are so selected that the sump temperature is lower than 85°, preferably lower than 80° C. When the distillation is carried out under reduced pressure, water is now obtained at the top of the column. In general, the hydrogen peroxide content in the aqueous distillate can be adjusted to less than 0.2% by weight without difficulty. However, it is also possible to control the distillation in such a way that the distillate contains less than 0.1% by weight of $H_2O_2$. Of course, constituents which are volatile with steam and are contained in the raffinate can also pass into the distillate. Thus, for example, small amounts of percarboxylic acid or carboxylic acid which have not been extracted can pass over, with the water, into the distillate. In general, the aqueous distillate contains less than 2% by weight of percarboxylic acid and less than 1% by weight of carboxylic acid.

An aqueous solution which essentially contains hydrogen peroxide is taken off at the second take-off weir as the first sidestream. The hydrogen peroxide content is generally between 2 and 40% by weight. Preferably, a solution which contains 10 to 30% by weight of $H_2O_2$ is taken off. The take-off of a 15 to 25% strength by weight hydrogen peroxide solution is very particularly preferred. The hydrogen peroxide contained in the first sidestream essentially corresponds to that amount of hydrogen peroxide which is contained in the smaller partial stream of the raffinate. In general, more than 60% of the hydrogen peroxide contained in the smaller partial stream of the raffinate can be recovered in this way. It is easily possible to recover more than 70% of the hydrogen peroxide. Usually, it is even possible to recover more than 80% of the hydrogen peroxide contained in the smaller partial stream. This hydrogen peroxide which has been recovered can be fed into the column below the first take-off weir, or, should a third take-off weir be present, below the latter. It can, for example, be fed into the column together with the larger partial stream. It can also be metered into the column separately from the larger partial stream. Of course, the hydrogen peroxide taken off in the first sidestream can also be utilised in other ways.

A second sidestream, which essentially contains the acid catalyst which is introduced into the column with the smaller partial stream, is taken from the column at the first take-off weir. This second sidestream can still contain amounts of hydrogen peroxide. In general these amounts are up to 25% of the hydrogen peroxide contained in the smaller partial stream of the raffinate. Preferably, the column is operated in such a way that the second sidestream contains less than 20% of the amounts of hydrogen peroxide originally present in the smaller partial stream. Per-compounds of the acid catalyst can also be present in this second sidestream, as in the smaller partial stream of the raffinate. When sulphuric acid is used as the acid catalyst, a minor amount of Caro's acid is present. The concentration of acid catalyst in the second sidestream can be regulated within wide limits by the sump temperature and by the pressure used. In general, the conditions are so selected that an aqueous solution containing about 20 to 70% by weight of the acid catalyst is obtained. This solution of the acid catalyst can be further worked up so that the acid catalyst can also be re-used for the present process or in other ways. Working up of this type can be effected, for example, by distillation. To make up the amounts of acid catalyst which are removed from the process with the second sidestream, it is possible to use, in addition to the acid catalyst which has been recovered by working up the second sidestream, also fresh acid catalyst. In principle, this amount of catalyst, which serves to replenish the amounts of catalyst withdrawn with the second sidestream, can be added at different points in the process. Thus, for example, this amount can be fed into the larger partial stream of the raffinate from the extraction before the distillation or can be fed into the product stream which is obtained after reconcentration of the raffinate from the extraction and is withdrawn from the sump of the distillation column. However, it is also possible to feed the catalyst, used for replenishment, into the reaction system in which the reaction of carboxylic acid with hydrogen peroxide to give percarboxylic acid takes place, in which case the catalyst can be dissolved wholly or partly in the carboxylic acid which passes into the reaction. The catalyst can also be replenished by adding the catalyst to the product stream which passes into the extraction system or by feeding it directly into the extraction system. The catalyst can be fed into the process in the pure form or in an aqueous solution, which optionally can also contain hydrogen peroxide, and in principle any desired concentration of the catalyst present in solution can be used. It is particularly advantageous to replenish the amounts of acid catalyst withdrawn with the second sidestream by an aqueous solution, containing hydrogen peroxide, of the acid catalyst.

A reconcentrated aqueous solution of hydrogen peroxide and the acid catalyst is obtained as the sump product from the column. In general, the procedure is such that the concentration of hydrogen peroxide and the acid catalyst is such that the sump product can be recycled directly into the reaction with carboxylic acid. If the fresh feed of hydrogen peroxide has not also been passed into the distillation unit, it can be added, after the distillation, to the reconcentrated raffinate, but it can also be fed into the reaction of carboxylic acid with hydrogen peroxide.

After reconcentration of the raffinate, an aqueous solution which contains about 20 to 40% by weight of hydrogen peroxide and about 15 to 40% by weight of acid catalyst is generally present in the sump of the distillation column. These concentrations can also be higher or lower than stated.

The reflux to the top of the column can be produced, for example, by condensation of the top vapours and division, in accordance with the reflux ratio, of the condensate and by returning the reflux flow to the top of the column. However, a certain reflux is also advisable below the first take-off weir since the vapours flowing through the first take-off weir should be substantially free from hydrogen peroxide. This reflux can now be produced, for example, by feeding either fresh water or a partial stream of the distillate obtained at the top of the column, in the requisite amount, to the column below the first take-off weir. However, in a further embodiment the reflux can also be produced by a partial condenser which is installed in the column below the first take-off weir. Since, however, the amount of vapours which are produced in the column below the first take-off weir and which reach the first take-off weir is in general much too large for recovery of the amount of $H_2O_2$ contained in the smaller partial stream, it is also possible, with this partial condenser, to condense such a large amount of vapour that only the minimum amount of vapour required for the desired recovery of $H_2O_2$ still remains and flows through the first take-off weir to the upper part of the column. However, with this mode of operation it is necessary to take off, via a third partial stream, the amount which makes up the difference between the total amount of condensate from the partial condenser and the requisite amount of reflux to the part of the column below the first take-off weir. The implementation of a partial stream take-off of this type is in itself known. For example, it can be carried out in such a way that the whole of the condensate from the partial condenser is collected in a third take-off weir of the previously described design and is fed to a reflux divider which operates either inside or outside the column. This optionally present third take-off weir is located below the first take-off weir. The distance of the two take-off weirs from one another is appropriately up to 2 theoretical plates.

The aqueous hydrogen peroxide, which is introduced into the process either before or after the distillation, is generally a commercially available hydrogen peroxide. The concentration of the hydrogen peroxide is not important for the process of the invention. In general, $H_2O_2$ in a concentration of from 5 to 90% by weight, preferably from 30 to 75% by weight, is used. Stabilisers can be added to the aqueous hydrogen peroxide. For example, stabilisers such as are mentioned in Gmelins Handbuch der anorganischen Chemie (Gmelins Handbook of Inorganic Chemistry), 8th edition, oxygen volume, section 7, 1966, page 2,274 and 2,275 can be used.

With regard to the distillation unit used to carry out the process according to the invention, the column will be designed as an integral unit. However, it is of course also possible to divide the distillation column into several parts and to arrange it, for example, as a two-part column. In such a case it is appropriate to make the division in such a way that it takes place at the first or second take-off weir. The vapours leaving one column section, comprising a distillation unit which is divided into one or more structural units, can be likewise compressed before introducing them into a second column section; this can be accomplished in a known manner by means of a vapour condensor. It is likewise feasible to carry out a vapour compression in a distillation unit in the form of a closed unit which is provided at an appropriate place in the column so that some column sections can be operated at different pressures.

Suitable materials for the distillation unit are glass, enamelled steels, teflon-lined steels, and high grade stainless steels which, in addition to iron, in the main also contain chromium and nickel. Tantalum or zirconium can be used. Zirconium is particularly suitable. Examples of high grade stainless steels which may be mentioned are a material with the DIN designation 1.4571, which, in addition to iron, contains 17.5% by weight of chromium, 11.5% by weight of nickel, 2.25% by weight of molybdenum, and also up to 2% by weight of manganese, up to 1% by weight of silicon, up to 0.1% by weight of carbon and small amounts of titanium, or a material which, in addition to iron, contains 25% by weight of chromium, 25% by weight of nickel, 2.25% by weight of molybdenum and up to 2% by weight of manganese, up to 1% by weight of silicon, up to 0.06% by weight of carbon and also small amounts of titanium and which is designated according to DIN by the number 1.4577. Other materials, for example aluminium, can also be used for those parts of the distillation column which do not come into contact with the acid catalyst.

In an industrial embodiment of the process according to the invention, an aqueous solution containing 25 to 35% by weight of hydrogen peroxide and 25 to 40% by weight of sulphuric acid is reacted with propionic acid at a molar ratio of hydrogen peroxide to propionic acid of 0.8 to 1.5. The equilibrium mixture formed is extracted with benzene. A benzene solution containing 15 to 22% by weight of perpropionic acid is obtained as the extract. The raffinate contains 8 to 15% by weight of hydrogen peroxide, 30 to 45% by weight of sulphuric acid, less than 0.3% by weight of perpropionic acid and less than 0.2% by weight of propionic acid.

Figure 1:
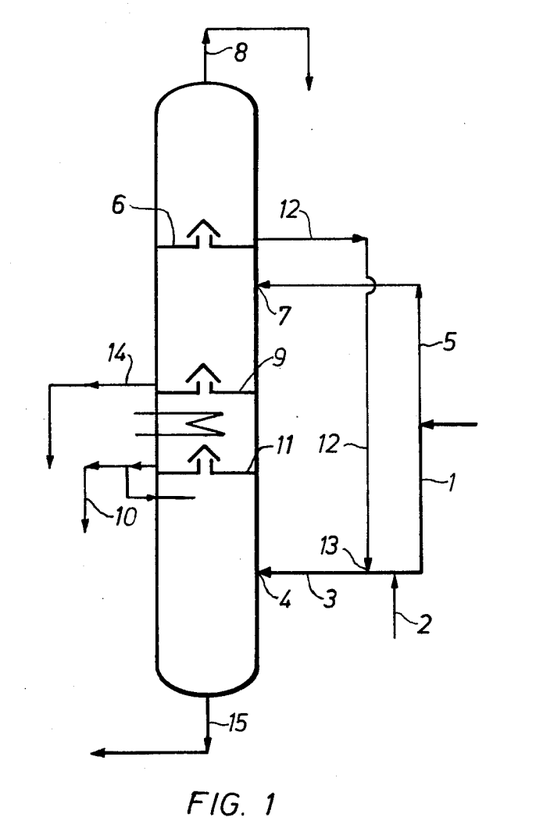
FIG. 1 is a schematic flow diagram showing a simplified method for carrying out the process of the invention.

This raffinate is divided in a ratio of 5:100 and further treated according to FIG. 1. Hydrogen peroxide, which is consumed largely in the reaction of $H_2O_2$ with propionic acid, is mixed, in the form of a commercially available 50% strength by weight aqueous solution, via line 2 into the large partial stream 1 and this mixture is fed via line 3 into the column according to the invention (see FIG. 1). The feed point 4 is in the vicinity of the sump. The smaller partial stream of the raffinate passes via line 5 into the part of the column located below the second take-off weir 6. The feed point 7 is located directly below the second take-off weir 6. A bubble cap tray column with 16 to 20 theoretical plates is used as the column and a falling flow evaporator is used as the evaporator. At a pressure below 150 mm Hg, water is obtained at the top of the column at 8. The total quantity of water obtained, which is withdrawn from the column, essentially corresponds to the quantity of water introduced into the process with the fresh hydrogen peroxide and that formed during the reaction of propionic acid to give perpionic acid. All of part of the water which is withdrawn is obtained at the top of the column. However, part of the water can also be withdrawn from the part 10 of the column which is located below the first take-off weir 9. For this purpose it is advisable to provide a further take-off wier 11 below the first take-off weir. The water which is obtained as the distillate at the top of the column and optionally as a 3rd sidestream 10 from a 3rd take-off weir 11 generally contains less than 0.1% by weight of $H_2O_2$ and about 0.5 to 1.0% by weight of perpropionic acid. The first sidestream 12 is taken off at the second take-off weir 6. It consists of an aqueous solution which contains 15 to 20% by weight of $H_2O_2$ and which is admixed to the larger partial stream of the raffinate at 13. A solution containing 30 to 60% by weight of sulphuric acid is taken off, as the second sidestream 14, at the first take-off weir 9. This second sidestream 14 contains about 5% by weight of hydrogen peroxide and about 5% by weight of Caro's acid. The take-off at the sump of the column, which is made via line 15, consists of an aqueous solution of 25 to 35% by weight of hydrogen peroxide and 25 to 40% by weight of sulphuric acid and is recycled into the reaction with propionic acid. The yield for perpropionic acid in benzene solution, relative to the hydrogen peroxide fed into the process, is more than 95%, this yield being independent of the period of operation of the circulation process.

The particular advantage of the process according to the invention is that the high initial yields of percarboxylic acid can be maintained throughout the entire period of operation of the process.

Figure 2:
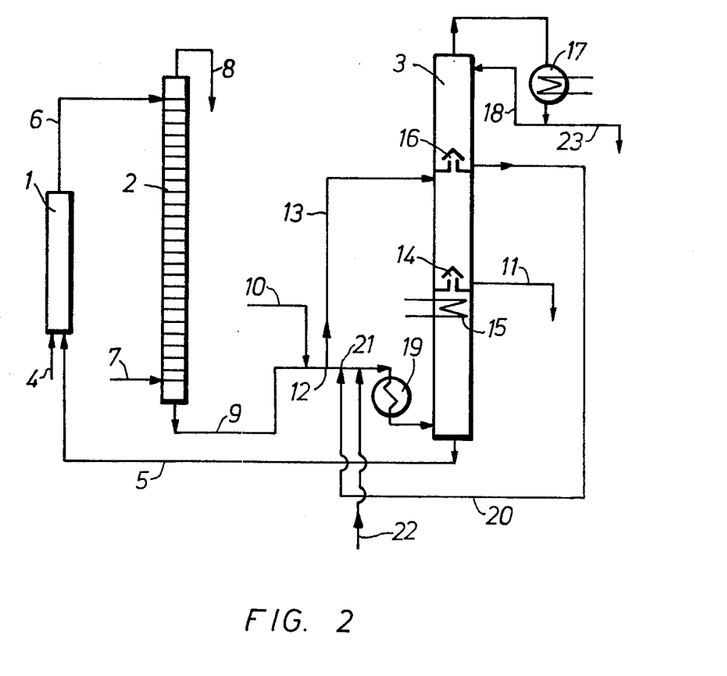
FIG. 2 is a schematic flow diagram showing a scheme similar to that of FIG. 1 in conjunction with a process for preparing perpropionic acid.

EXAMPLE 1 (SEE FIG. 2)

The apparatus used, which is shown in FIG. 2, comprises a reaction system 1, an extraction system 2 and a distillation unit 3. The reaction system 1 consists of a delay tube 50 cm in length and 4.5 cm in diameter, which can be heated and is provided with packing. A pulsed sieve tray column, which is provided with 80 sieve trays and has a length of 4 m and a diameter of 25 mm, is used as the extraction system 2.

When the apparatus is operated continuously, 183.5 g per hour of propionic acid are fed via line 4 to the delay tube 1. An aqueous solution, which contains 31.4% by weight of hydrogen peroxide and 35.5% by weight of sulphuric acid, is also introduced, in an amount of 268.4 g per hour, via line 5 into the delay tube 1, which is warmed to 38° C. In this aqueous solution, which is withdrawn from the sump of the distillation column 3, part of the hydrogen peroxide and of the sulphuric acid contained therein is present as Caro's acid. In the following text, this amount of Caro's acid is calculated as sulphuric acid and hydrogen peroxide and recorded accordingly. The same procedure is also followed with the other product streams from the process, which contain sulphuric acid and hydrogen peroxide. In the delay tube, the mixture consisting of propionic acid, sulphuric acid, hydrogen peroxide and water, is warmed to 38° C for about 20 minutes, 60% of the propionic acid being converted into perpropionic acid, so that the product stream which leaves the delay tube 1 via line 6 in an amount of 451.9 g per hour has the following composition: 29.63% by weight of perpropionic acid, 16.24% by weight of propionic acid, 21.09% by weight of sulphuric acid, 7.46% by weight of hydrogen peroxide and 25.58% by weight of water. This solution containing perpropionic acid is cooled to 20° C and then fed into the upper part of the extraction column 2, where it is extracted with benzene in counter-current. The benzene is fed, in an amount of 458 g per hour, via line 7 into the lower part of column 2. 666 g per hour of a 20.03% strength by weight benzene solution of perpropionic acid, which, in addition to the perpropionic acid, still contains 10.99% by weight of propionic acid as well as 0.09% by weight of hydrogen peroxide and 0.1% by weight of water, is taken off at the top of column 2 via line 8. An aqueous solution which has the following composition: 13.56% by weight of hydrogen peroxide, 39.06% by weight of sulphuric acid, 0.2% by weight of perpropionic acid, 0.08% by weight of propionic acid and 47.1% by weight of water, is obtained as the raffinate from the extraction. The raffinate, which is obtained in an amount of 244 g per hour, is withdrawn from the sump of the extraction column 2 via line 9. 35 g of a 10% strength by weight aqueous solution of sulphuric acid are fed, via line 10, into the stream of raffinate in order to replenish the amount of sulphuric acid which is withdrawn from the process per hour via line 11. The raffinate 9, increased by the product stream 10, is now divided at 12 in a ratio of 27.9 : 1, after which the smaller stream is fed in an amount of 10 g per hour, via line 13, to the distillation column 3.

The distillation unit 3 consists of a bubble cap tray column with a total of 18 theoretical plates and a diameter of 5 cm. A first take-off weir 14 is installed between the 5th and 6th plate, calculated from the sump; a condenser 15 is located below their weir. A further take-off weir 16 is installed in the column between the 13th and 14th plate, again counted from the sump. The condenser 17 serves to condense the top vapours. The reflux to the column is fed to the top of the column via line 18 in an amount of 7.8 g/hour. The column is heated by means of a falling film evaporator 19. The sump temperature of the column, which is operated at a pressure of 60 mm Hg, is 75° C. A temperature of 45° C is set up at the top of the column.

The smaller partial stream of the raffinate from the extraction, which is fed via line 13 to column 3, is passed into the column directly below the take-off weir 16. An aqueous 13.38% strength by weight solution of hydrogen peroxide is withdrawn, in an amount of 8 g per hour, from this take-off weir 16 via line 20 and combined with the larger partial stream of the raffinate divided at 12. 104.9 g per hour of a 50% strength by weight aqueous solution of hydrogen peroxide ( 52.44 g. of $H_2O_2 \triangleq$ 1.54 mols) are then added via line 22 to the product stream which results after the feed point 21. The mixture, which now contains 22.37% by weight of hydrogen peroxide, 24.95% by weight of sulphuric acid, 52.48% by weight of water as well as 0.12% by weight of perpropionic acid and 0.05% by weight of propionic acid, is then introduced, in an amount of 381.9 g per hour, via evaporator 19 into the sump of the column. The vapours leaving the lower part of the column are partially condensed at the condenser 15. The amount condensed here is about 35 g per hour and is fed as reflux to the lower part of the column, that is to say the part of the column located below the take-off weir 14. 9.9 g per hour of a 35.4% strength by weight aqueous sulphuric acid solution which, in addition to the sulphuric acid, still contains 1.01% by weight of hydrogen peroxide, are taken off at the take-off weir 14 via line 11 and withdrawn from the process. 106 g per hour of water, which contains 0.67% by weight of perpropionic acid, are obtained as the top product, which is obtained after the condenser 17 and is withdrawn via line 23. 268.4 g per hour of an aqueous solution, which contains 35.5% by weight of sulphuric acid and 31.4% by weight of hydrogen peroxide, are withdrawn from the sump of the column via line 5 and returned to the reaction system 1. The yield of perpropionic acid is 96.1%, relative to the hydrogen peroxide employed in the process. 91.45% of the hydrogen peroxide contained in the smaller partial stream of the raffinate 13 are recovered and fed back into the process via stream 20.

Figure 3:
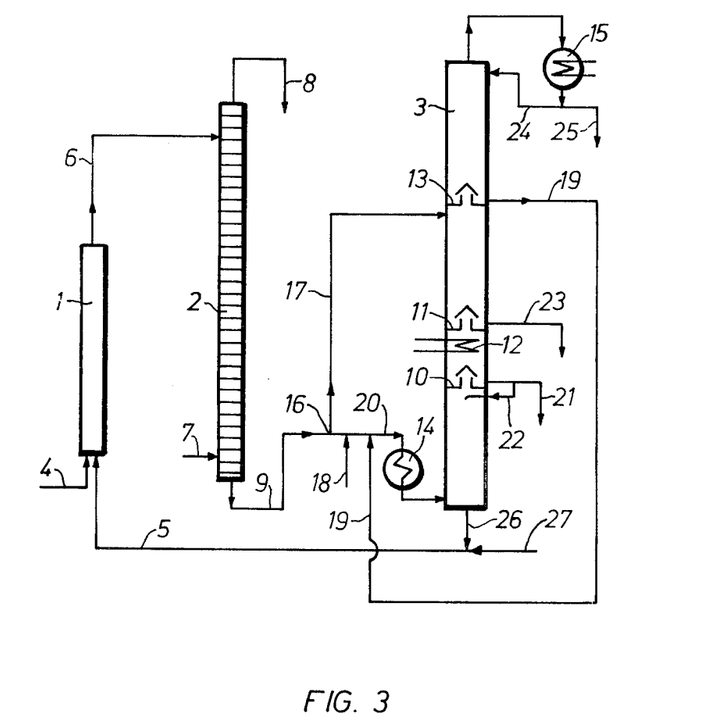
FIG. 3 is a schematic flow diagram similar to FIG. 2 showing a variant thereof in which two side cuts are taken.

EXAMPLE 2 (see also FIG. 3)

An apparatus arrangement, which is illustrated by FIG. 3 and which consists of a reaction system 1, an extraction system 2 and a distillation unit 3 is used. The apparatuses described in Example 1 are used as the reaction system 1 and the extraction system 2, the dimensions being those indicated in Example 1. The amounts and compositions of the product streams conveyed in 4, 5, 6, 7, 8 and 9 are also unchanged with respect to Example 1. Small amounts of Caro's acid, which is formed by a partial reaction of the sulphuric acid with the hydrogen peroxide with liberation of water, can be present in the product streams which contain sulphuric acid and hydrogen peroxide. These amounts of Caro's acid are again calculated and taken into acount in the quantity and concentration data as though they were present in the form of hydrogen peroxide and sulphuric acid.

The distillation unit 3 again consists of a bubble cap tray column with a total of 18 theoretical plates and a diameter of 5 cm. Two take-off weirs 10 and 11 are installed between the 5th and 6th plate, calculated from the sump, and the condenser 12 is located between these weirs. A further third take-off 13 is arranged 8 plates above the take-off weir 11 and this corresponds to the take-off weir 13 being arranged between the 13th and 14th plate, calculated from the sump of the column. The column is heated by means of a falling film evaporator 14. The condenser 15 serves to condense the top vapours from the column. A temperature of 45° C is set up at the top of the column, which is operated at a pressure of 60 mm Hg. A temperature of 74° to 75° C is measured in the sump of the column.

The raffinate from the extraction, which leaves the extraction column 2 via 9, is divided at 16 in a ratio of 26.2 : 1 into a smaller and a larger product stream and the smaller stream is then fed, in an amount of 9 g per hour, via 17 into the column immediately below the take-off weir 13. 136 g per hour of a 38.65% strength by weight aqueous solution of hydrogen peroxide (= 52.55 g of $H_2O_2$ = 1.546 mols) and 3.8 g per hour of the mixture which is taken off at takeoff weir 13 and which, in addition to water, contains 29.06% by weight of hydrogen peroxide, are added, via 18 and via 19 respectively, to the larger product stream obtained after dividing the raffinate. The mixture which now results and which contains 24.5% by weight of sulphuric acid, 22.82% by weight of hydrogen peroxide and 52.5% by weight of water as well as 0.12% by weight of perpropionic acid and 0.05% by weight of propionic acid, is fed via 20, in an amount of 375 g per hour, to the evaporator 14 and then passes into the sump of the distillation column 3. The vapours flowing upwards through the take-off weir 10 are partially condensed at the condenser 12, so that part of the quantity of water to be withdrawn from the process can be taken off at the take-off weir 10. 81.6 g per hour of water, which contains 0.68% by weight of perpropionic acid as well as traces of hydrogen peroxide, are now taken off at this take-off weir 10 via 21. The reflux for the part of the column located below the take-off weir 10 is fed, in an amount of 35 g per hour, to this part of the column via 22 directly below the take-off weir 10. 10 g per hour of an aqueous solution which, in addition to 35% by weight of sulphuric acid, still contains 1.2% by weight of hydrogen peroxide, are taken off at take-off weir 11 and this solution is removed from the process via 23. The vapours which issue at the top of the column are condensed in condenser 15 and fed, in an amount of 3.4 g per hour, via 24 to the top of the column as reflux for the part of the column located above take-off weir 13, whilst 24.4 g per hour of a 0.74% strength aqueous solution of perpropionic acid are withdrawn via 25. 264.9 g per hour of a solution which contains 34.65% by weight of sulphuric acid, 31.82% by weight of hydrogen peroxide and 33.52% by weight of water are withdrawn from the sump of the column via 26 and then combined with 3.5 g per hour of sulphuric acid, which is added via 27. The amount of sulphuric acid which is added serves to make up the amount of sulphuric acid which has been withdrawn from the process with the stream 23. The product stream which now results after the streams 26 and 27 have been combined consists of an aqueous solution which contains 31.4% by weight of hydrogen peroxide and 35.5% by weight of sulphuric acid and is recycled, in an amount of 268.4 g per hour, via 5 into the reaction system 1.

The yield of perpropionic acid in the benzene extract which is withdrawn, in an amount of 666 g per hour, from the top of extraction column 2 via 8 is 95.9%, relative to the hydrogen peroxide employed in the process. There is a 90.1% recovery of the hydrogen peroxide contained in the smaller partial stream of the raffinate, that is to say 90.1% of the amount of hydrogen peroxide fed into the column in stream 17 are found again in stream 19.

Figure 4:
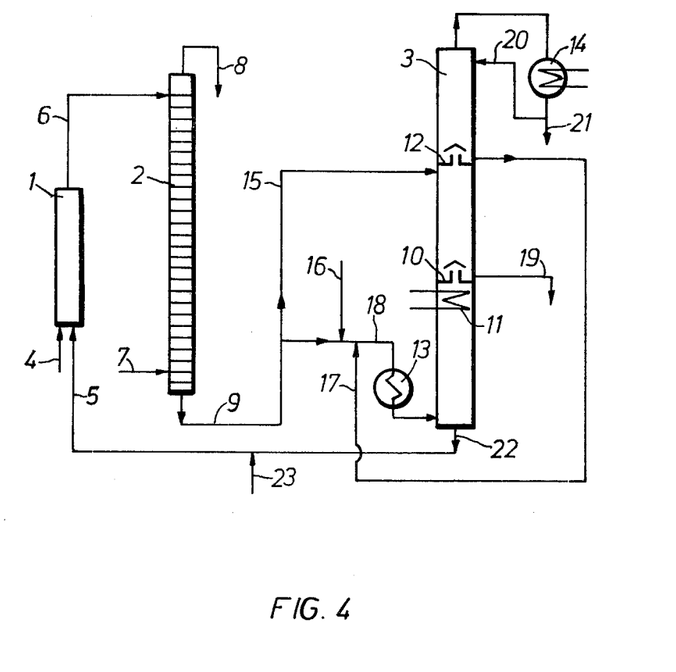
FIG. 4 is a schematic flow diagram similar to FIG. 3 showing a still further embodiment of the invention.

EXAMPLE 3 (see also FIG. 4)

The arrangement of apparatus used consists, as in Examples 1 and 2, of a reaction system 1, an extraction system 2 and the distillation unit 3 and is shown in FIG. 4. The reactor 1 and the extraction column 2 have the dimensions indicated in Example 1 and are operated under the conditions mentioned in Example 1. The quantity and composition of the product streams 4, 5, 6, 7, 8 and 9 are also unchanged with respect to Example 1.

A bubble cap tray which has 20 theoretical plates and a diameter of 5 cm and in which a first take-off weir 10 is installed between the 6th and 7th plate, calculated from the sump, is used as the distillation column 3. A condenser 11 is arranged below this take-off weir 10. A second takeoff weir 12 is located 9 plates above the take-off weir 10. The column, which is operated at a pressure of 60 mm Hg, is heated by means of the falling flow evaporator 13. The temperature at the top is 44° C and the sump temperature is 75° C. The vapours which issue at the top of the column are condensed by means of condenser 14.

The raffinate from the extraction, which is withdrawn in an amount of 244 g per hour from the sump of the extraction column 2 via 9 is divided in a ratio of 9.6 : 1 into a larger and a smaller stream. The smaller partial stream 15 is fed, in an amount of 22.9 g/hour, into the column directly below the take-off weir 12. 88.26 g per hour of a 50% strength by weight aqueous solution of hydrogen peroxide and 12 g/hour of the mixture which is withdrawn from take-off weir 12 and which, in addition to water, contains 23.92% by weight of hydrogen peroxide are added, via 16 and via 17 respectively, to the larger partial stream of the raffinate. The mixture which is obtained after these streams have been combined and which contains 23.96% by weight of hydrogen peroxide, 26.86% by weight of sulphuric acid as well as 0.15% by weight of perpropionic acid, 0.06% by weight of propionic acid and 48.97% by weight of water, is fed, in an amount of 321.4 g per hour, via 18 to evaporator 13 and then passes into the sump of column 3. The vapours emanating from the sump are partially condensed at condenser 11, so that 36 g per hour can be fed as reflux to the part of the column located below condenser 11. 25.7 g per hour of an aqueous solution containing 34.9% by weight of sulphuric acid and 0.93% by weight of hydrogen peroxide are withdrawn at take-off weir 10 and are removed from the process via 19. The vapours issuing at the top of the column are condensed by means of condenser 14. 11 g per hour of the distillate obtained after condenser 14 are fed as reflux via 20 to the part of the column located above take-off weir 12, whilst 62.8 g/hour of a 1.13% strength by weight aqueous solution of perpropionic acid are taken off via 21. An aqueous solution which contains 35.55% by weight of sulphuric acid and 31.33% by weight of hydrogen peroxide is withdrawn, in an amount of 242.9 g per hour, from the sump of the column via 22. In order to replenish, in the process, the amounts of sulphuric acid withdrawn from the process with product stream 19, 25.5 g per hour of an aqueous solution which, in addition to 35.12% by weight of sulphuric acid, also contains 32.14% by weight of hydrogen peroxide, are added via 23 to the mixture taken from the sump of the column. The mixture which results after product streams 22 and 23 have been combined and which contains 35.5% by weight of sulphuric acid and 31.4% by weight of hydrogen peroxide as well as 33.1% by weight of water is recycled, in an amount of 268.4 g per hour, via 5 into the reactor 1.

The yield of perpropionic acid in the benzene extract, which is withdrawn from the extraction column via 8, is 96.3% relative to the total hydrogen peroxide introduced into the process via the streams 16 and 23. 92.3% of the hydrogen peroxide contained in the smaller partial stream of the raffinate is recovered, as is shown by comparison of the amounts of hydrogen peroxide contained in stream 15 and in stream 17.

We claim:

1. In the process for continuous production of a solution of an aliphatic percarboxylic acid in an organic solvent which is immiscible with water by contacting aqueous hydrogen peroxide with the carboxylic acid corresponding to said percarboxylic acid, said carboxylic acid having 1 to 4 carbon atoms, in the presence of a water soluble acid catalyst selected from the group consisting of sulfuric acid, phosphoric acid, a phosphonic acid, a phosphinic acid, an acid salt of sulfuric acid, an acid salt of phosphoric acid, a sulfonic acid, a chlorinated sulfonic acid, a fluorinated sulfonic acid and a mixture thereof for the reaction to produce the percarboxylic acid and water in a reaction mixture comprising the percarboxylic acid, water, catalyst and unreacted hydrogen peroxide, extracting the reaction mixture with said organic solvent for take-up of the percarboxylic acid by the organic solvent to provide said solution of percarboxylic acid, and provide an aqueous raffinate rich in hydrogen peroxide and catalyst, distilling the aqueous raffinate, to remove water therefrom and provide a concentrated raffinate, and recycling the concentrated raffinate to said contacting, the improvement which comprises said acid catalyst having a boiling point above 160° C and said distillation being performed at a pressure below 250 mm Hg and a sump temperature of less than 85° C, by:
   (a) dividing the raffinate produced by the extraction into two streams in a ratio of 1 to 25 : 100 to provide a larger raffinate stream and a smaller raffinate stream,
   (b) distilling said streams under reduced pressure in a distillation column which has at least two take-off weirs as tray inserts, the first take-off weir being at least two theoretical plates above the sump, the second take-off weir being arranged at least two theoretical plates above the first take-off weir and the section of column between the second take-off weir and the top of the column having at least two theoretical plates,
   (c) the larger raffinate stream being introduced into the column below the first take-off weir and the smaller raffinate stream being introduced into the column below the second take-off weir,
   (d) water being removed as overhead product of the distillation,
   (e) a first sidestream, which essentially contains the hydrogen peroxide from the smaller raffinate stream being withdrawn from the second take-off weir which is a 2 to 40% by weight aqueous solution of hydrogen peroxide,
   (f) a second sidestream being withdrawn from the first take-off weir, which is an aqueous solution of the acid catalyst substantially free of hydrogen peroxide, and
   (g) concentrated aqueous solution of hydrogen peroxide and acid catalyst being collected in the sump of the column as said concentrated raffinate and withdrawing and recycling the concentrated raffinate to said contacting.

2. Process of claim 1, wherein said ratio is 2–8 : 100.

3. Process of claim 1, wherein said ratio is 4 – 6 : 100.

4. Process of claim 1, wherein the concentration of acid catalyst in the raffinate is 10 to 50% by weight.

5. Process of claim 1, wherein the section of the column which extends from the sump up to the first take-off weir has 3 – 20 theoretical plates.

6. Process of claim 1, wherein the second take-off weir is 3 – 20 theoretical plates above the first take-off weir.

7. Process of claim 1, wherein said overhead product contains less than 0.2% by weight of hydrogen peroxide.

8. Process of claim 1, wherein said overhead product contains less than 2% by weight of percarboxylic acid and carboxylic acid.

9. Process of claim 1, wherein the first side stream contains 15 – 25% by weight of hydrogen peroxide.

10. Process of claim 1, wherein the second side stream contains 20 – 70% by weight of acid catalyst.

11. Process of claim 1, wherein the concentrated raffinate collected in the sump contains 20 to 40% by weight of hydrogen peroxide and 15 to 40% by weight of acid catalyst.

12. Process of claim 1, wherein the aqueous raffinate contains 8 to 15% by weight of hydrogen peroxide, 30 to 45% by weight of acid catalyst, less than 0.3% by weight of perpropionic acid and less than 0.2% by weight of propionic acid.

13. Process of claim 1, wherein the third take-off weir is disposed not more than 2 theoretical plates below the first take-off weir, and a third sidestream is taken from the third take-off weir.

14. Process of claim 1, wherein the first sidestream is introduced into the distillation column with said larger stream.

15. Process of claim 1, wherein the solvent is not miscible with water and is virtually inert towards hydrogen peroxide, the percarboxylic acid, and the acid catalyst.

16. Process of claim 15, wherein the catalyst is sulphuric acid and the solvent is benzene.

17. Process of claim 15, wherein the carboxylic acid is propionic acid.

18. Process according to claim 1 wherein said organic solvent is an aliphatic, cycloaliphatic or aromatic hydrocarbon or chlorinated hydrocarbon or an ester of a carboxylic acid.

19. Process according to claim 1 wherein said solvent is selected from the group consisting of n-pentane, iso-octane, cyclohexane, benzene, toluene, xylene, methylene chloride, chloroform, 1,2-dichloroethane, 1,2-dichloropropane, methyl acetate, ethyl acetate, n-propyl acetate, isopropyl acetate, n-butyl acetate, isoamyl acetate, methyl propionate, ethyl propionate, propyl propionate, butyl propionate and chlorobenzene.

20. A process according to claim 1 wherein said distillation column is made of tantalum or zirconium.

* * * * *

UNITED STATES PATENT AND TRADEMARK OFFICE
CERTIFICATE OF CORRECTION

PATENT NO. : 4,088,676
DATED : May 9, 1978
INVENTOR(S) : Willi Hofen et al

It is certified that error appears in the above–identified patent and that said Letters Patent are hereby corrected as shown below:

Column 7, line 67, "fof" should read -- for --.

Column 11, line 66, "their" should read -- this --.

Column 12, line 16, after "(" insert -- $\hat{=}$ --.

*Signed and Sealed this*

*Twenty-fourth* Day of *October 1978*

[SEAL]

*Attest:*

RUTH C. MASON
*Attesting Officer*

DONALD W. BANNER
*Commissioner of Patents and Trademarks*